US00PP16539P3

(12) United States Plant Patent
Bradford

(10) Patent No.: US PP16,539 P3
(45) Date of Patent: May 16, 2006

(54) NECTARINE TREE NAMED 'VIKING PEARL'

(50) Latin Name: *Prunus persica*
Varietal Denomination: Viking Pearl

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 278 days.

(21) Appl. No.: 10/746,675

(22) Filed: Dec. 29, 2003

(65) Prior Publication Data

US 2005/0144692 P1 Jun. 30, 2005

(51) Int. Cl.
*A01H 5/00* (2006.01)

(52) U.S. Cl. ..... Plt./188

(58) Field of Classification Search ..... Plt./188
See application file for complete search history.

(56) References Cited

U.S. PATENT DOCUMENTS

PP9,358 P 11/1995 Bradford

*Primary Examiner*—Howard J. Locker

(57) ABSTRACT

The present invention relates to a nectarine tree and more particularly to a new and distinct variety broadly characterized by a medium size, vigorous, hardy, self-fertile, productive and regular bearing tree. The fruit matures under the ecological conditions described approximately the last week in July, with first picking on Jul. 26, 2003. The fruit is uniformly large in size, excellent in flavor, globose in shape, clingstone in type, very firm in texture, white in flesh color, and red in skin color. The variety was developed as an open pollinated seedling from an unnamed white flesh nectarine.

1 Drawing Sheet

Botanical classification: *Prunus persica.*
Variety denomination: 'Viking Pearl'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Viking Pearl'. During the spring and summer of 1997 I gathered fruit from several different nectarine trees located in my experimental orchard near Le Grand, Calif., in Merced County (San Joaquin Valley). One particular group of nectarines were white in flesh color, clingstone in type, and sub-acidic in flavor, and were thus designated as "WNC (OP)". The seeds from this fruit were removed, cracked, stratified, germinated and grown as seedlings on their own root in my greenhouse, and upon reaching dormancy transplanted to a cultivated area in the experimental orchard described above. During the fruit evaluation season of 2000 I selected the present variety as a single tree from the group of "WNC (OP)" described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to 'Fire Pearl' (U.S. Plant Pat. No. 9,358) nectarine, by producing nectarines that are clingstone in type, globose in shape, nearly full red in skin color, white in flesh color, very firm in texture, and sub-acidic and sweet in flavor, but is distinguished therefrom by having a small blossom instead of a large showy blossom and by producing fruit that is much larger in size.

SUMMARY OF VARIETY

In summary, the present variety is characterized by a medium size, vigorous, hardy, self-fertile, productive and regular bearing tree. The fruit matures under the ecological conditions described approximately the last week in July, with first picking on Jul. 26, 2003. The fruit is uniformly large in size, excellent in flavor, globose in shape, clingstone in type, very firm in texture, white in flesh color, and red in skin color. The variety was developed as an open pollinated seedling from an unnamed white flesh nectarine.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 1, 2003, on the original tree during its sixth growing season. All major color code designations are by reference to the Inter-Society Color Council, National Bureau of Standards. Common color names are also used occasionally.

TREE

Size: Medium, reaching a height of 9' [2.7 m.] and a spread of 8' [2.4 m.] after six growing seasons utilizing typical dormant pruning.

Vigor: Medium, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-fertile.

Bearing: Regular bearer with no alternate bearing yet observed.

Trunk:

*Size.*—Medium, with a maximum diameter of 2⅝" [66.7 mm.] after the sixth growing season.

*Texture.*—Shaggy.

*Bark color.*—Dark grayish reddish brown [47. d.gy.rBr].

*Lenticels.*—Approximate Number Per Square Inch: 8. Color: Light Brown [57. l.Br]. Average Size: ⅛" to ⅜" [3.2–9.5 mm.].

Branches:

*Size.*—Diameter of limb is 1½" [38.1 mm.] measured 12" above the crotch, typical of *Prunus persica,* and dependent upon cultural practices and climatic conditions.

*Texture.*—Smooth on first year wood, increasing roughness with age.

*Color.*—1st Year Wood Topside: Dark pink [6. d.Pk]. 1st Year Wood Underside: Brilliant yellow green [116. brill.YG]. Older Wood: Deep brown [56. deep Br].

*Lenticels.*—Approximate Number Per Square Inch: 30. Color: Light brown [57. l.Br]. Typical size: 1/16" to 3/16" [1.6–4.8 mm.].

Leaves:

*Size.*—Large. Average Length: 6" [152 mm.]. Average width: 1⅝" [41 mm.].

*Arrangement.*—Alternate.

*Thickness.*—Medium.

*Form.*—Elliptical.

*Apex.*—Acuminate.

*Base.*—Acute, with an average base angle of 75 degrees.

*Surface.*—Smooth.

*Color.*—Dorsal Surface: Dark yellowish green [137. d.yG]. Ventral Surface: Moderate yellowish green [136. m.yG].

*Margin.*—Finely serrate.

*Venation.*—Pinnately net veined.

*Vein color.*—Light yellow green [119. l.YG].

*Petiole.*—Average Length: 7/16" [11.1 mm.]. Average Thickness: 1/16" [1.6 mm.]. Color: Brilliant yellow green [116. brill.YG].

*Stipules.*—Number: 2 per young leaf, up to 6 per growing tip. Average Length: ⅜" [9.5 mm.]. Color: Brilliant yellow green [116. brill.YG] when young, becoming Dark grayish reddish brown [47. d.gy.rBr] with age.

*Glands.*—Number: Usually 2. Position: Alternate, usually positioned on the petiole very close to the blade. Size: Medium. Form: Globose. Color: Brilliant yellow green [116. brill.YG] when young becoming Light reddish brown [42. l.rBr] in the center with age.

*Leaf buds.*—Small, conic.

Flower buds:

*Hardiness.*—Hardy, with respect to central California winters.

*Diameter.*—Typically ¼" [6.4 mm.] 1 week before bloom.

*Length.*—Typically ⅜" [9.5 mm.] 1 week before bloom.

*Form.*—Not appressed.

*Surface.*—Pubescent.

*Color.*—Moderate purplish red [258. m.pR].

Flowers: Perfect, complete, perigynous, usually a single pistil, typically 24–28 or more stamens, five sepals and petal locations alternately positioned.

*Type.*—Small.

*Average flower diameter.*—15/16" [23.8 mm.].

*Number of petals.*—Five, no double blossom observed.

*Petal shape.*—Oval.

*Petal margin.*—Wavy.

*Average petal diameter.*—⅜" [9.5 mm.].

*Average petal length.*—9/16" [14.3 mm.].

*Petal apex.*—Rounded.

*Petal base.*—Acute.

*Petal color.*—Pale purplish pink [252. p.pPk] toward the apex with Moderate purplish red [258. m.pR] toward the margin.

*Anther color.*—Dark reddish orange [38. d.rO] over a Brilliant orange yellow [67. brill.OY] center.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—½" [12.7 mm.].

*Average stamen length.*—7/16" [11.1 mm.].

*Fragrance.*—Moderate.

*Blooming period.*—A few days earlier than average.

*Onset of bloom.*—One percent on Feb. 24, 2003.

*Date of full bloom.*—Mar. 5, 2003.

*Duration of bloom.*—One to two weeks, dependent on ambient temperature.

*Number per cluster.*—1 to 2 with single flowers most common.

FRUIT

Maturity when described: Firm ripe, Aug. 1, 2003.

Date of first picking: Jul. 26, 2003.

Date of last picking: Aug. 6, 2003.

Size: Uniform, large.

*Average diameter axially.*—2⅞" [73.0 mm.].

*Average diameter across suture plane.*—2⅞" [73.0 mm.].

*Typical weight.*—9.0 ounces [255 grams].

Form: Globose, uniform.

*Longitudinal section form.*—Circular to somewhat oval.

*Transverse section through diameter.*—Circular.

Suture: A sharp groove near the base becoming a moderate groove extending well beyond the apex with a moderate depression at the pistil point.

Ventral surface: Rounded, lipped stronger toward the apex.
Lips: Somewhat unequal.
Cavity: Flaring, elongated in suture plane, suture showing on one side, Pale yellow green [121. p.YG] stem markings typical.
*Depth.*—5/8" [15.9 mm.].
*Breadth.*—1" [25.4 mm.].
Base: Rounded to truncate.
Apex: Rounded.
Pistil point: Apical, negligible in length, depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in the dry season.
*Color.*—Very deep red [14. v.deep R] smoothly blending to Dark pink [6. d.Pk] with minimal Light orange yellow [70. l.OY] freckling toward the apex.
Flesh:
*Color.*—Purely White [263. White] toward the skin with Deep red [13. deep R] streaking only within 1/4" [6.4 mm.] of the stone.
*Surface of pit cavity.*—Very deep red [14. v.deep R] to Deep pink [3. deep Pk] fibers breaking when twisted from the stone.
*Amygdalin.*—Scarce.
*Juice.*—Abundant, rich.
*Texture.*—Firm, crisp.
*Fibers.*—Abundant, fine.
*Ripens.*—Slightly earlier toward the apex.
*Flavor.*—Subacid and sweet, ranging 16 to 21 brix.
*Aroma.*—Very slight.
*Eating quality.*—Very good.

STONE

Type: Clingstone.
Form: Oval.
Hilum: Narrow.
Base: Straight.
Apex: Acute, but not sharp.
Sides: Equal.
Surface: Irregularly furrowed toward the apex, pitted toward the base.
Ridges: Jagged toward the base.
External color of stone: Dark yellowish brown [78. d.yBr] when dry.
Surface color of stone cavity: Deep yellowish brown [75. deep yBr].
Average pit wall thickness: 1/4" [6.4 mm.].
Average width: 1 1/8" [28.6 mm.].
Average length: 1 9/16" [39.7 mm.].
Average breadth: 7/8" [22.2 mm.].
Tendency to split: None observed.
Kernel:
*Form.*—Oval.
*Skin color.*—Pale yellow [89. p.Y] when freshly removed.
*Pellicle color.*—Grayish yellowish brown [80. gy.yBr].
*Vein color.*—Grayish yellowish brown [80. gy.yBr].
*Taste.*—Bitter.
*Viable.*—Yes.
*Average width.*—9/16" [14.3 mm.].
*Average length.*—13/16" [20.6 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Fire Pearl' (U.S. Plant Pat. No. 9,358) nectarine by producing nectarines that are clingstone in type, globose in shape, nearly full red in skin color, white in flesh color, very firm in texture, and sub-acidic and sweet in flavor, but is distinguished therefrom by having a small blossom instead of a large showy blossom and by producing fruit that is much larger in size.

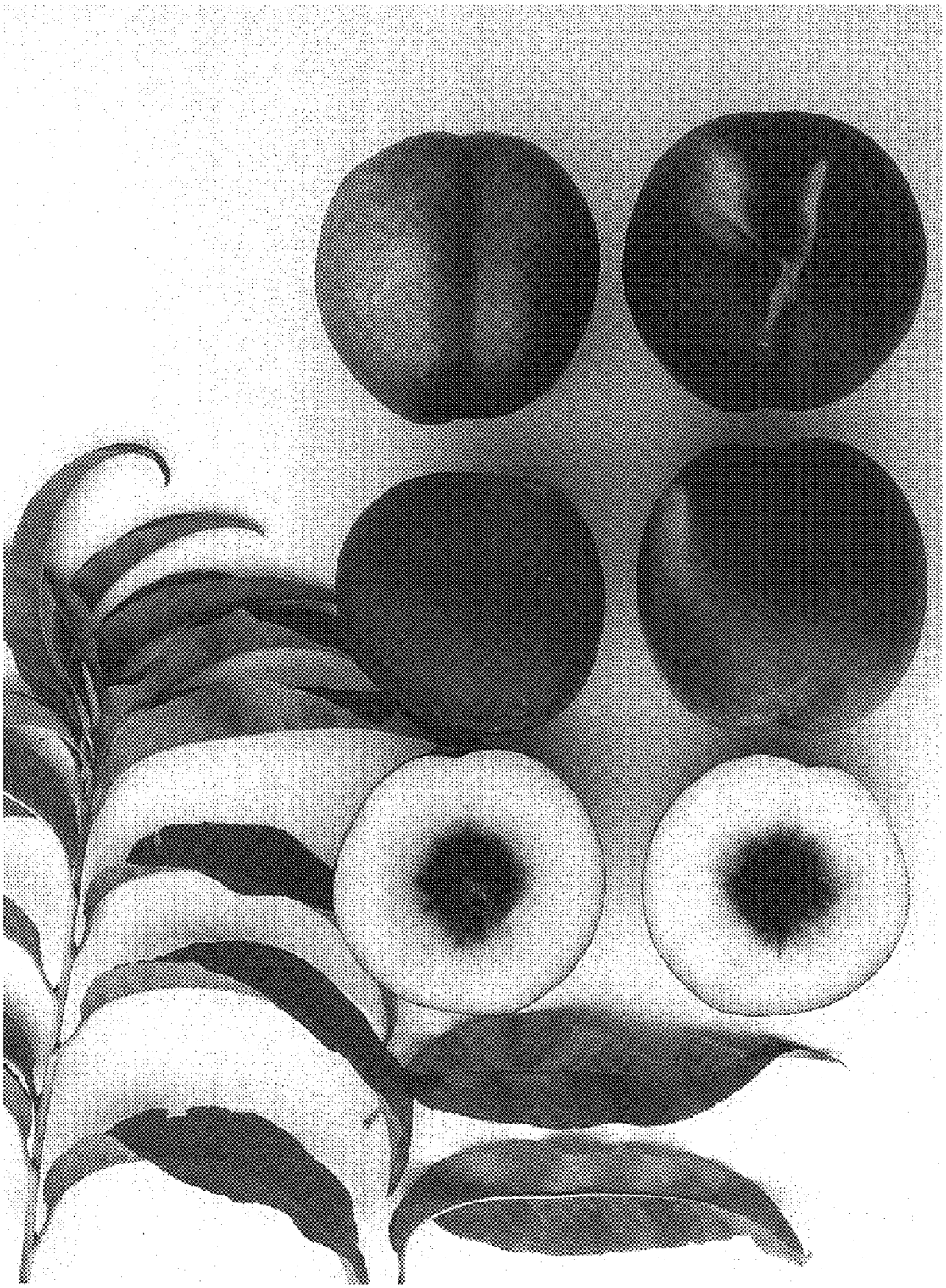

* * * * *